(12) United States Patent
Liao et al.

(10) Patent No.: US 8,895,777 B2
(45) Date of Patent: Nov. 25, 2014

(54) COMPOUNDS AND COMPOSITIONS FOR DELIVERING ACTIVE AGENTS

(75) Inventors: Jun Liao, Yorktown Heights, NY (US); Pingwah Tang, Elmsford, NY (US); David Gschneidner, Thornwood, NY (US); Jonathan Maeyer, Tucson, AZ (US)

(73) Assignee: Emisphere Technologies Inc, Roseland, NJ (US)

( * ) Notice: Subject to any disclaimer, the term of this patent is extended or adjusted under 35 U.S.C. 154(b) by 0 days.

(21) Appl. No.: 12/439,425

(22) PCT Filed: Aug. 29, 2007

(86) PCT No.: PCT/US2007/077100
§ 371 (c)(1),
(2), (4) Date: Apr. 17, 2009

(87) PCT Pub. No.: WO2008/027958
PCT Pub. Date: Mar. 6, 2008

(65) Prior Publication Data
US 2010/0015088 A1    Jan. 21, 2010

Related U.S. Application Data

(60) Provisional application No. 60/841,723, filed on Aug. 31, 2006.

(51) Int. Cl.
| | | |
|---|---|---|
| C07C 59/00 | (2006.01) |
| A61K 31/192 | (2006.01) |
| C07C 59/68 | (2006.01) |
| A61K 38/27 | (2006.01) |
| A61K 31/00 | (2006.01) |
| C07C 59/90 | (2006.01) |
| A61K 38/28 | (2006.01) |
| A61K 47/12 | (2006.01) |
| A61K 9/00 | (2006.01) |

(52) U.S. Cl.
CPC ............. *A61K 31/192* (2013.01); *A61K 9/0095* (2013.01); *C07C 59/68* (2013.01); *A61K 9/0019* (2013.01); *A61K 38/27* (2013.01); *A61K 31/00* (2013.01); *C07C 59/90* (2013.01); *A61K 38/28* (2013.01); *A61K 47/12* (2013.01)
USPC ...................................................... 562/471

(58) Field of Classification Search
None
See application file for complete search history.

(56) References Cited

U.S. PATENT DOCUMENTS 5,447,728 A    9/1995  Milstein et al.
5,451,410 A    9/1995  Milstein et al.
(Continued)

FOREIGN PATENT DOCUMENTS

DE         1155139 B      10/1963
WO      WO-9834632 A1    8/1998
(Continued)

OTHER PUBLICATIONS

Database Caplus Chemical Abstracts Service, Columbus, Ohio, US; Database Accession No. 1960:119345, Abstract of Gowing et al., Botanical Gazette (Chicago) (1960), 121, 143-51.*

(Continued)

*Primary Examiner* — Karl J Puttlitz
(74) *Attorney, Agent, or Firm* — Blank Rome LLP

(57) ABSTRACT

The present invention provides delivery agent compounds, compositions containing delivery agent compounds and an active agent and methods for delivering active agents, such as biologically or chemically active agents.

23 Claims, 10 Drawing Sheets

(56) References Cited

U.S. PATENT DOCUMENTS

| | | |
|---|---|---|
| 5,541,155 A | 7/1996 | Leone-Bay et al. |
| 5,629,020 A | 5/1997 | Leone-Bay et al. |
| 5,643,957 A | 7/1997 | Leone-Bay et al. |
| 5,650,386 A | 7/1997 | Leone-Bay et al. |
| 5,693,338 A | 12/1997 | Milstein |
| 5,709,861 A | 1/1998 | Santiago et al. |
| 5,766,633 A | 6/1998 | Milstein et al. |
| 5,773,647 A | 6/1998 | Leone-Bay et al. |
| 5,776,888 A | 7/1998 | Leone-Bay et al. |
| 5,792,451 A | 8/1998 | Sarubbi et al. |
| 5,804,688 A | 9/1998 | Leone-Bay et al. |
| 5,811,127 A | 9/1998 | Milstein et al. |
| 5,840,340 A | 11/1998 | Milstein et al. |
| 5,863,944 A | 1/1999 | Leone-Bay et al. |
| 5,866,536 A | 2/1999 | Leone-Bay et al. |
| 5,876,710 A | 3/1999 | Leone-Bay et al. |
| 5,879,681 A | 3/1999 | Leone-Bay et al. |
| 5,935,601 A | 8/1999 | Leone-Bay et al. |
| 5,939,381 A | 8/1999 | Leone-Bay et al. |
| 5,955,503 A | 9/1999 | Leone-Bay et al. |
| 5,958,457 A | 9/1999 | Santiago et al. |
| 5,965,121 A | 10/1999 | Leone-Bay et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,071,538 A | 6/2000 | Milstein et al. |
| 6,090,958 A | 7/2000 | Leone-Bay et al. |
| 6,100,298 A | 8/2000 | Leone-Bay et al. |
| 6,180,140 B1 | 1/2001 | Leone-Bay et al. |
| 6,242,495 B1 | 6/2001 | Leone-Bay et al. |
| 6,245,359 B1 | 6/2001 | Milstein et al. |
| 6,313,088 B1 | 11/2001 | Leone-Bay et al. |
| 6,344,213 B1 | 2/2002 | Leone-Bay et al. |
| 6,358,504 B1 | 3/2002 | Leone-Bay et al. |
| 6,391,303 B1 | 5/2002 | Haas et al. |
| 6,399,798 B2 | 6/2002 | Gschneidner et al. |
| 6,428,780 B2 | 8/2002 | Leone-Bay et al. |
| 6,461,643 B2 | 10/2002 | Milstein et al. |
| 6,525,020 B2 | 2/2003 | Leone-Bay et al. |
| 6,558,706 B2 | 5/2003 | Kantor et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,693,208 B2 | 2/2004 | Gscheidner et al. |
| 6,699,467 B2 | 3/2004 | Leone-Bay et al. |
| 6,846,844 B2 | 1/2005 | Tang |
| 6,900,344 B2 | 5/2005 | Bernadino et al. |
| 6,916,489 B2 | 7/2005 | Milstein et al. |
| 6,960,355 B2 | 11/2005 | Leone-Bay et al. |
| 6,972,300 B2 | 12/2005 | Leone-Bay et al. |
| 6,991,798 B1 | 1/2006 | Gschneidner et al. |
| 7,005,141 B2 | 2/2006 | Milstein et al. |
| 7,067,119 B2 | 6/2006 | Leone-Bay et al. |
| 7,071,214 B2 | 7/2006 | Sarubbi et al. |
| 7,084,279 B1 | 8/2006 | Gschneidner |
| 7,115,663 B2 | 10/2006 | Moye-Sherman et al. |
| 7,125,910 B2 | 10/2006 | Leone-Bay et al. |
| 7,129,274 B1 * | 10/2006 | Leone-Bay et al. .......... 514/571 |
| 7,138,546 B2 | 11/2006 | Tang |
| 7,151,191 B2 | 12/2006 | Boyd et al. |
| 7,169,776 B2 | 1/2007 | Bernadino et al. |
| 7,186,414 B2 | 3/2007 | Gschneidner et al. |
| 7,208,483 B2 | 4/2007 | Milstein et al. |
| 7,217,703 B2 | 5/2007 | Gschneidner |
| 7,262,325 B2 | 8/2007 | Bay et al. |
| 7,279,597 B1 | 10/2007 | Leone-Bay et al. |
| 7,297,794 B2 | 11/2007 | Gschneidner et al. |
| 7,351,741 B2 | 4/2008 | Weidner et al. |
| 7,384,982 B2 | 6/2008 | Bay et al. |
| 7,390,834 B2 | 6/2008 | Moye-Sherman et al. |
| 7,411,084 B2 | 8/2008 | Bernadino |
| 7,495,030 B2 | 2/2009 | Gschneidner |
| 7,544,833 B2 | 6/2009 | Bay et al. |
| 7,553,872 B2 | 6/2009 | Sarubbi et al. |
| 7,662,771 B2 | 2/2010 | Herr et al. |
| 7,700,775 B2 | 4/2010 | Liao et al. |
| 7,744,910 B2 | 6/2010 | Gschneidner et al. |
| 2005/0148497 A1 | 7/2005 | Khan |

FOREIGN PATENT DOCUMENTS

| | | |
|---|---|---|
| WO | WO-0007979 A2 | 2/2000 |
| WO | WO-0059863 A1 | 10/2000 |
| WO | WO-0132596 A1 | 5/2001 |
| WO | WO-0220466 A1 | 3/2002 |
| WO | WO-03072195 A2 | 9/2003 |
| WO | WO-2004006907 A1 | 1/2004 |
| WO | WO-2005112937 A1 | 12/2005 |
| WO | WO-2006084164 A2 | 8/2006 |

OTHER PUBLICATIONS

Database Caplus Chemical Abstracts Service, Columbus, Ohio, US; Database Accession No. 1962:475650, Abstract of Eckstein et al., Przemysl Chemiczny (1961), 49(No. 5), 275-9.*

Database Caplus Chemical Abstracts Service, Columbus, Ohio, US; Database Accession No. 1979:415175, Abstract of Takematsu et al., JP 54023125.*

Database Caplus Chemical Abstracts Service, Columbus, Ohio, US; Database Accession No. 1958:11742, Abstract of Webley et al., Journal of General Microbiology (1958), 18, 733-46.*

Database Caplus Chemical Abstracts Service, Columbus, Ohio, US; Database Accession No. 1959:11694, Abstract of GB 793740.*

Database Caplus Chemical Abstracts Service, Columbus, Ohio, US; Database Accession No. 1961:100075, Abstract of Fawcett et al., Proceedings of the Royal Society of London, Series B: Biological Sciences (1959), 150, 95-119.*

Database Caplus Chemical Abstracts Service, Columbus, Ohio, US; Database Accession No. 1990:423671, Abstract of Freedman et al., Journal of Heterocyclic Chemistry (1989), 26(6), 1547-54.*

Database Caplus Chemical Abstracts Service, Columbus, Ohio, US; Database Accession No. 1988:570822, Abstract of Kwapiszewski et al., Acta Poloniae Pharmaceutica (1987), 44(2), 121-31.*

Database Caplus Chemical Abstracts Service, Columbus, Ohio, US; Database Accession No. 1979:41517, Abstract of JP 54023125.*

Database Caplus Chemical Abstracts Service, Columbus, Ohio, US; Database Accession No. 1964:16426, Abstract of Toepel et al., DE 1155139, Oct. 3, 1963.*

Faulkner et al., Journal of the Chemical Society [Section] C: Organic (1966), (9), 884-7.*

Inamori T, et al., Absorpotion Enhancement of Argatroban by Medium Chain Fatty Acid Sodium Salts, Proceedings of the Controlled Release Society, 1997 US, No. 24, 1997, pp. 283-284.

Zeiger et al., Aryloxyalkanoic acids, their esters and cycling products as pesticide-active compounds, Wissenschaftliche Zeitschrift der Paedagogischen Hochschule Karl Liebknecht Potsdam (1977), 21(1), 29-46. CAS online citation 89:163182, retreived from STN; Columbus, OH, USA.

Oniscu et al., Kinetic study of the esterification of gamma-phenoxybutyric acids with ethyl alcohol, Revistade Chimie (1984), 35(7), 591-2. STN online citation 102:94983, retrieved from STN; Columbus, OH, USA.

* cited by examiner

Figure 3: Argatroban Administration in Rats

Figure 5. Argatroban Administration in Rats: Oral Groups

Figure 7.

Reference Nos. Used in Figures 1-6

| Code | Delivery Agent Compound |
|---|---|
| A | 8-[(2-hydroxybenzoyl)amino]octanoic acid |
| BB | 2-[4-[(2-hydroxybenzoyl)amino]phenyl]acetic acid |
| B | 10-[(2-hydroxybenzoyl)amino]decanoic acid |
| F | 8-[(5-chloro-2-hydroxybenzoyl)amino]octanoic acid |

JJ 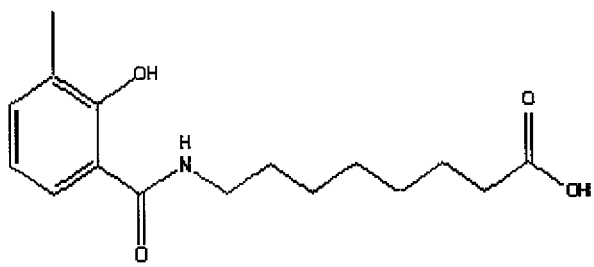
KK 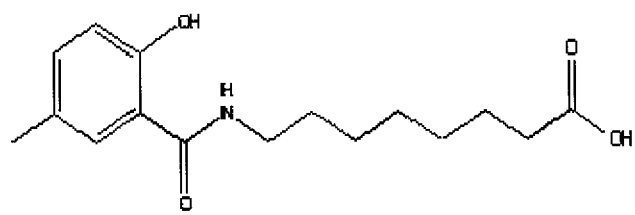
C 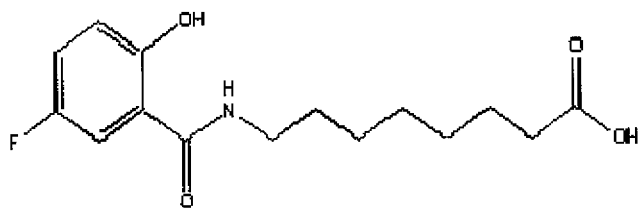
D 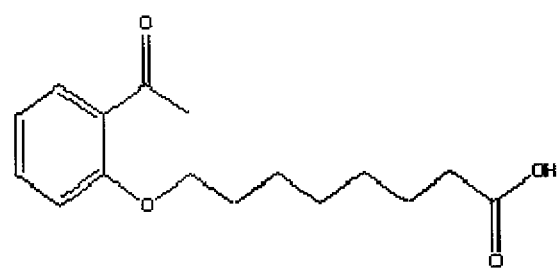
H 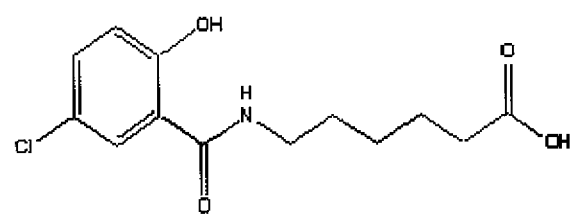

CC 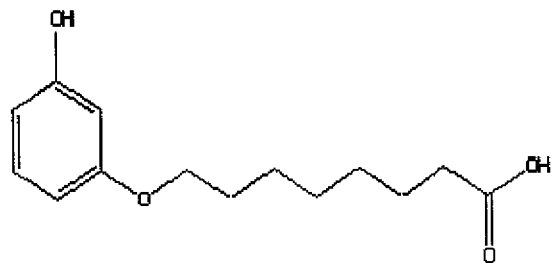
K 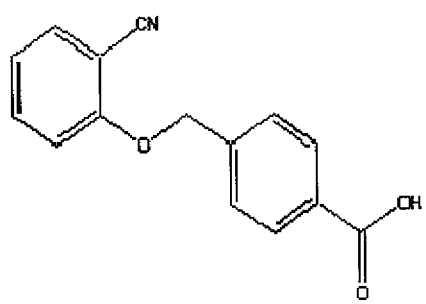
DD 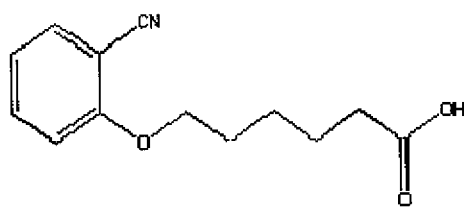
M 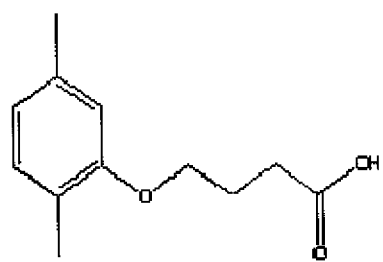
O 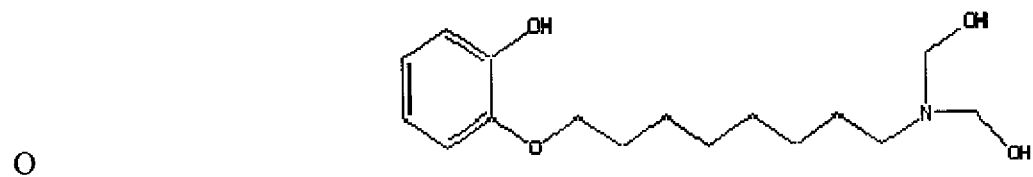

R 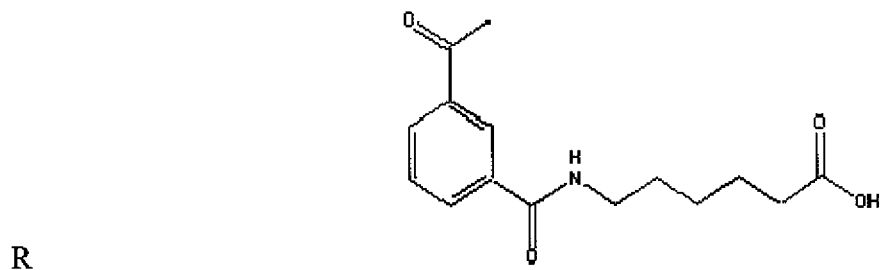
T 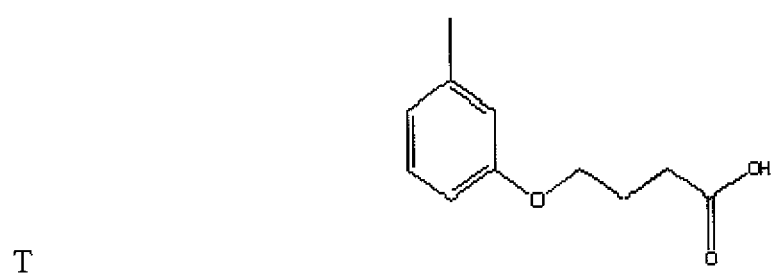
U 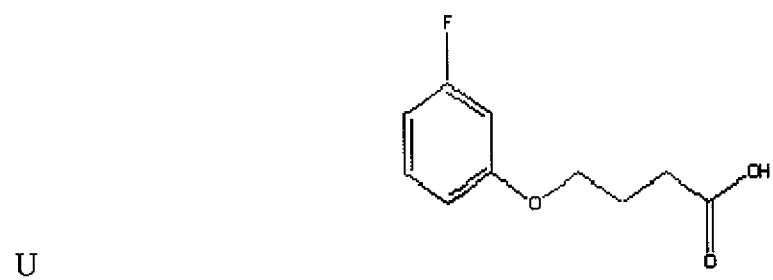
LL 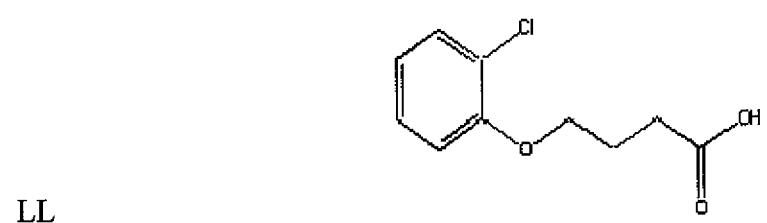

COMPOUNDS AND COMPOSITIONS FOR DELIVERING ACTIVE AGENTS

CROSS-REFERENCE TO PRIOR APPLICATIONS

This is a U.S. National Phase Application under U.S.C. §371 of International Patent Application No. PCT/US2007/077100 filed Aug. 29, 2007, which claims the benefit of U.S. Provisional Application No. 60/841,723, filed Aug. 31, 2006. The International Application re-published in English on Aug. 21, 2008 as WO2008/027958 under Article 21(2).

PRIORITY

The present invention claims the priority of U.S. Application No. 60/841,723, filed on 31 Aug. 2006.

FIELD OF THE INVENTION

The present invention relates to compounds, compositions and methods for delivering active agents, such as biologically or chemically active agents.

BACKGROUND OF THE INVENTION

Conventional means for delivering active agents are often severely limited by biological, chemical and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are also imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin ihibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention relates to compounds (hereafter referred to as "delivery agent compounds") that facilitate the delivery of active agents. The delivery agent compound of the present invention may be selected from the group consisting of:

Compound 1

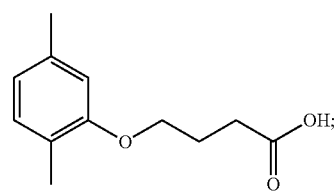

Compound 2

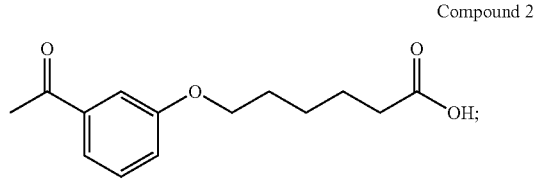

Compound 3

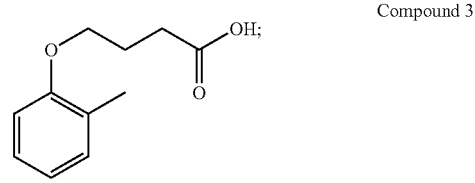

Compound 4

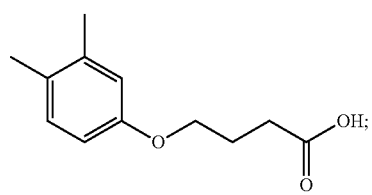

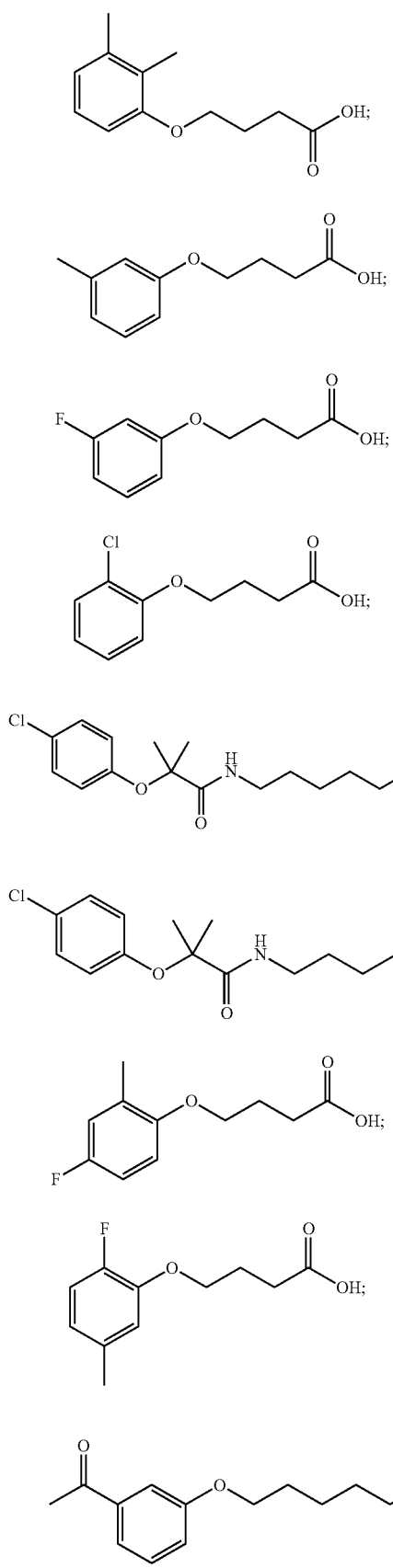
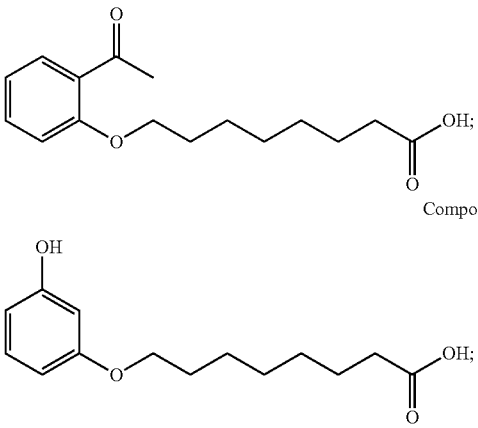

and pharmaceutically acceptable salts thereof.

Mixtures of these delivery agent compounds may also be used.

The invention also provides a composition (e.g., pharmaceutical compositions) comprising at least one of the delivery agent compounds, and at least one active agent. These compositions deliver active agents to biological systems with increased or improved bioavailability of the active agent compared to administration of the active agent without the delivery agent compound.

Also provided is a dosage unit form comprising the composition of the present invention. The dosage unit form may be in the form of a liquid or a solid, such as a tablet, capsule or particle, including a powder or sachet.

Another embodiment is a method for administering an active agent to an animal, particularly an animal in need of the active agent, by administering a composition comprising at least one of the delivery agent compounds and the active agent to the animal. Preferred routes of administration include the oral and intracolonic routes.

Yet another embodiment is a method of treating a disease or for achieving a desired physiological effect in an animal by administering an effective amount of the composition of the present invention.

Yet another embodiment is a method of preparing a composition of the present invention by mixing at least one delivery agent compound of the formulas above, and at least one active agent.

BRIEF DESCRIPTION OF THE DRAWINGS

FIG. 7 contains the references of compounds used in FIGS. 1-6.

DETAILED DESCRIPTION OF THE INVENTION

Delivery Agent Compounds

Figure 1:
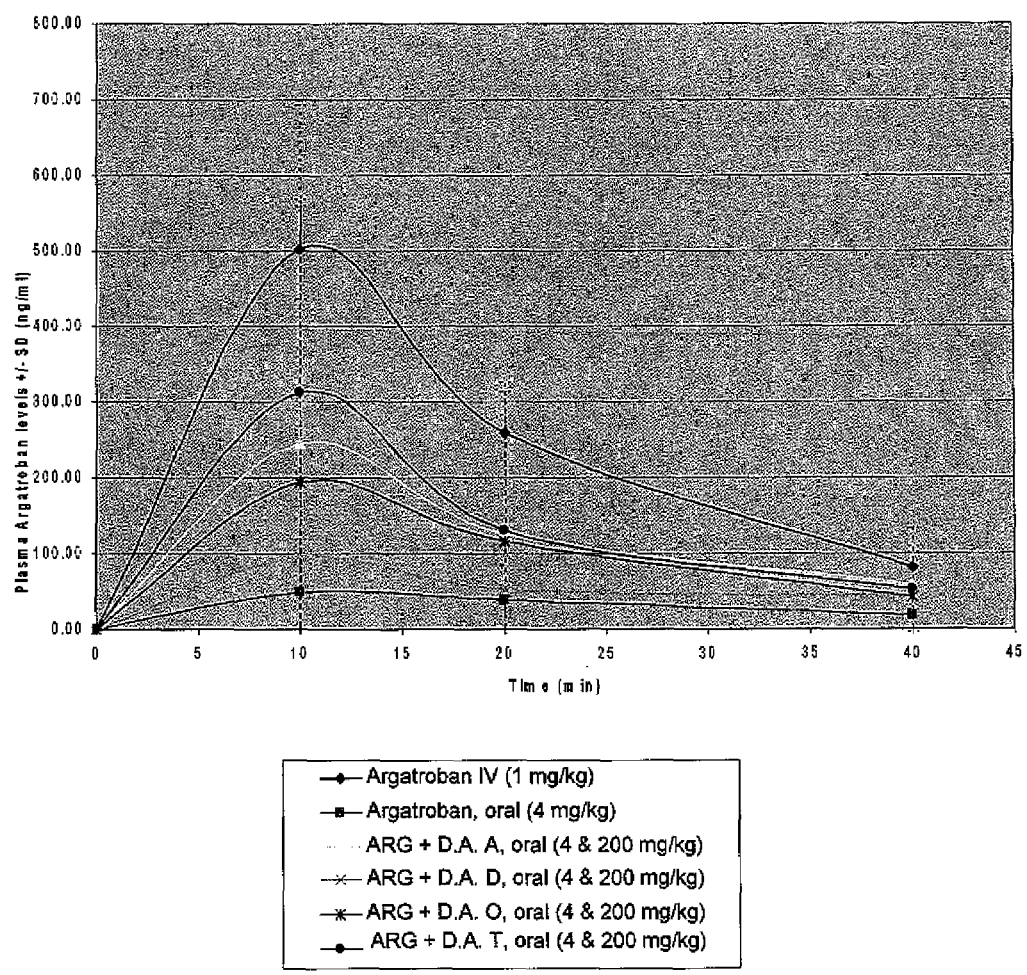
FIGS. 1-6 are graphs of plasma argatroban concentrations in male, Sprague-Dawley rats versus time after intravenous and oral administration of argatroban without a delivery agent, and oral administration of argatroban with delivery agent compounds of the present invention.

The delivery agent compound (e.g. 4-(2,5-dimethylphenoxy)butyric acid) may be in the form of its free acid or salts thereof such as pharmaceutically acceptable salts. Suitable salts include, but are not limited to, organic and inorganic salts, for example, ammonium, acetate salt, citrate salt, halide (preferably hydrochloride), alkali metal (e.g., sodium and potassium), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, sodium, citrate and mesylate salts. The salts may also be solvates, including ethanol solvates, and hydrates.

Salts of the delivery agent compounds of the present invention may be prepared by methods known in the art. For example, citrate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptan, ethyl acetate, acetonitrile, acetone, methanol, and tetrahydrofuran (THF) and mixtures thereof Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH—NHCH$_7$—, —CH$_2$NHC(O)—, —OC(O)NHCH$_2$—, —CH$_2$NHCOCH$_2$O—, —OCH$_2$C(O)NHCH$_2$—, —NHC(O)OH$_2$O—, —OCH$_2$C(O)NH—, —NH—, —O—, and carbon-carbon bond. According to one embodiment, the polymeric delivery agent is not a polypeptide or polyamino acid. Such polymer-delivery agent conjugates and methods for preparing them are described in International Published Application No. WO 00/40203, which is hereby incorporated by reference. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastrointestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α (e.g., interferon alfacon-1 (available as Infergen® from InterMune, Inc. of Brisbane, Calif.)), β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastitn; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; glucagon-like peptide 1 (GLP-1); argatroban; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternatively, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may also be in the form of a solid, such as a tablet, capsule or particle, such as a powder or sachet. Solid dosage forms may be prepared by mixing the solid form of the compound with the solid form of the active agent. Alternatively, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the delivery agent compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as any one of the diseases or conditions listed in the table below, in an animal by administering the composition of the present invention. Preferably, an effective amount of the composition for the treatment or prevention of the desired disease or for achieving the desired physiological effect is administered. Specific indications for active agents can be found in the The Physicians' Desk Reference ($58^{th}$ Ed., 2004, Medical Economics Company, Inc., Montvale, N.J.), and Fauci, A S, et. al., Harrison's Principles of Internal Medicine ($14^{th}$ Ed., 1998, McGraw-Hill Health Professions Division, New York. Both of these references are herein incorporated by reference in their entirety. The active agents in the table below include their analogs, fragments, mimetics, and polyethylene glycol-modified derivatives (e.g., the PEGylated derivative of granulocyte colony stimulating factor sold as Neulasta®).

| Active Agent | Disease and Physiological Effect |
| --- | --- |
| Growth hormones (including human recombinant growth hormone and growth-hormone releasing factors and its analogs) | Growth disorders |
| Interferons, including α, β and γ | Viral infection, including chronic cancer, hepatitis, and multiple sclerosis |
| Interleukins (e.g. Interleukin-1; interleukin-2) | Viral infection; cancer; cell mediated immunity; and transplant rejection; |
| Insulin; Insulin-like growth factor IGF-1 | Diabetes |
| Immune Globulins, such as IVIg | smallpox, rabies, and diphtheria, Alzheimer's Disease; Primary immunodeficiencies; Acute Guillain-Barré syndrome; Chronic idiopathic demyelinating polyneuropathy (CIDP); Myasthenia gravis, polymyositis, and dermatomyositis; neonatal immune thrombocytopenia, heparin-induced thrombocytopenia, and antiphospholipid antibody syndrome: Posttransfusion purpura. |

-continued

| Active Agent | Disease and Physiological Effect |
|---|---|
| Heparin | Treatment and Prevention of Thrombosis, including (Deep Vein Thrombosis); prevention of blood coagulation |
| Calcitonin | Osteoporosis; diseases of the bone; bone pain; analgesic (including pain associated with osteoporosis or cancer) |
| Erythropoietin, Pegylated erythropoietin. | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in connection with Alzheimer's disease, Type II diabetes, and other amyloid-based diseases |
| Monoclonal antibodies | To prevent graft rejection; cancer; used in assays to detect diseases |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; Leutinizing Hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) and their Pegylated forms | shorten the duration of chemotherapy-induced neutropenia and thus treat or prevent infection in chemotherapy patients; Inhibit the growth of or to kill *Mycobacterium Intracellular Avium* Infection (MAC) |
| RNAi | Huntington, Alzheimers, Viral Infections (HIV, Hepatitis A, B or C, RSV), Cancers; Macular Degeneration |
| Prostaglandins | Hypertension |
| Cyclosporin | Transplant rejection; psoriasis, inflammatory alopecias; Sjogren's syndrome; Keratoconjunctivitis Sicca |
| Vasopressin | Nocturnal Enuresis; antidiuretic |
| Cromolyn sodium; | Asthma; allergies |
| Vancomycin | Treat or prevent antimicrobial-induced infections including, but not limitted to methacillin-resistant *Staphaloccccus aureus* and *Staph. epidermiditis* |
| gallium salts (such as gallium nitrate) | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of *mycobacterium* species, including but not limited to *mycobacterium tubercolosis*, and *mycobacterium avium* complex |
| Desferrioxamine (DFO) | Iron overload |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, |

-continued

| Active Agent | Disease and Physiological Effect |
|---|---|
| | and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| BIBN4096BS - (1-Piperidinecarboxamide•N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-•[R-(R*,S*)]-) | Anti-migraine; calcitonin gene- related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| GLP-1, Exendin - 3, Exendin - 4, Obestatin | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| acyclovir | Used to treat herpes infections of the skin, lip and genitals; herpes zoster (shingles); and chickenpox |
| HIV Entry Inhibitors (e.g. Fuzeon) | Inhibit entry of HIV into host cells |
| Sumatriptin, almotriptan, naratriptan, rizatriptan, frovatriptan and eletriptan (piperidinyloxy)phenyl, (piperidinyloxy)pyridinyl, (piperidinylsulfanyl)phenyl and (piperidinylsulfanyl)pyridinyl compounds | anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | Antivirals |
| Peptide YY (PYY) and PYY-like Peptides (e.g. PYY[3-36]) | Obesity, Diabetes, Eating Disorders, Insulin-Resistance Syndromes |

For example, one embodiment of the present invention is a method for treating a patient having or susceptible to diabetes by administering insulin in a pharmaceutical formulation of the present invention. Other active agents, including those set forth in the above table, can be used in conjunction with the pharmaceutical formulations of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

EXAMPLES

The following examples illustrate the present invention without limitation.

Example 1

Preparation of 4-(2,5-Dimethylphenoxy)butyric acid (Compound 1)

2,5-Dimethylphenol (6.1 g, 0.05 mol) and ethyl bromobutyrate were dissolved in 60 ml of N,N-Dimethylacetamide (DMAC). Potassium carbonate (11 g) and potassium iodide 0.5 g (0.003 mol) were added to this solution. The mixture was stirred at 70-80° C. for 24 hours. The filtrate was added to distilled water (200 ml). An oily precipitate formed and was extracted with methylene chloride (100 ml). The organic layer was washed with 5% sodium carbonate (3×150 ml), dried over anhydrous sodium sulfate, and concentrated to give al oily residue. The oil was dissolved in ethanol (5 ml). The solution was mixed with 2N sodium hydroxide (30 ml). The mixture was stirred at 70-80° C. until the ester was hydrolyzed (determined by HPLC). The solution was acidified with 3N hydrochloride to pH 1 to form a precipitate. The precipitate was collected by filtration and dissolved in 4% sodium bicarbonate. Insoluble materials were removed by filtration. The filtrate was acidified to pH 1 to form a precipitate. The precipitate was collected by filtration and air-dried. 6.6 g of 4-(2,5-dimethylphenoxy) butyric acid was recovered. Melting point: 63-65° C. Combustion analysis: % C. 69.21 (calcuated), 69.04 (found); % H, 7.74 (calculated); 7.49 (found). 1H NMR Analysis (d6-DMSO). δ 6.98, d, 1H; 6.71, s, 1H; 6.62, d, 1H; 3.94, t, 2H; 2.40, t, 2H; 2.24, s, 3H; 2.09, s, 3H; 1.95, p, 2H.

Example 2

Preparation of 4-(2,5-Dimethylphenoxy)butyric acid (Compound 1)

2,5-dimethylphenol (24.5 g, 0.2 mol) was dissolved in 125 ml of anhydrous ethanol. To the solution was added 75 ml of 21 wt % sodium ethoxide solution in ethanol (0.2 mol). The mixture solution was stirred at room temperature for 10 min. Ethyl 4-bromobutyrate (40 g, 0.205 mol) was then added to the solution. The reaction mixture was refluxed at 80° C. for 24 h. The precipitate was filtered off. The filtrate was then mixed with a solution of sodium hydroxide (10 g, 0.25 mol) in 150 ml of water. The mixture was stirred at 70° C. for about 2 hours, monitored with HPLC. It was diluted with 150 ml of water and acidified to pH 1. Oily precipitate formed immediately. It was collected by decanting the supernatant and washed with water twice (100 ml×2). The oily precipitate solidified after kept in water at room temperature overnight.

The precipitate was dissolved in 250 ml of water at pH 8-9. Any insoluble substance was filtered off. The filtrate was extracted with ethyl acetate twice (100 ml×2). The aqueous solution was acidified to pH 1. Precipitate formed immediately as oil, which solidified in about 2 hours. The precipitate was collected by filtration, washed thoroughly with water and dried in air. 22.9 g of 4-(2,5-dimethylphenoxy)-butyrate were recovered. Melting point: 63-65° C. Combustion analysis: % C, 69.21 (Calc'd); 69.13 (Found); % H, 7.74 (Calc'd); 7.62 (Found); 1H NMR analysis (d6-DMSO): δ 6.98, d, 1H; 6.71, s, 1H; 6.62, d, 1H; 3.94, t, 2H; 2.40, t, 2H; 2.24, s, 3H; 2.08, s, 3H; 1.95, p, 2H.

Example 3

Preparation of 6-(3-Acetylphenoxy)hexanoic acid (Compound 2)

A round bottom flask equipped with a magnetic stirrer bar and a reflux condenser was charged with 5.0 g (36.7 mmol) of 3-hydroxyacetophenone, 8.18 g (36.7 mmol) of ethyl 6-bromohexanoate and 50 mL of ethanol. The clear reaction mixture was treated with potassium carbonate (6.03 g, 44.0 mmol) and heated to reflux. After stirring for 24 hr at reflux, the reaction mixture was cooled to 25° C., filtered through a Celite pad and concentrated. The residue was taken up in of ethanol and treated with 15 mL of 2N aqueous sodium hydroxide (30 mmol). The reaction mixture was stirred for 6 hr at 25° C., before the ethanol was stripped off. The residue was acidified with aqueous 1N hydrochloric acid. The resulting solid was isolated by filtration and purified by recrystallization from ethanol/water to yield an off-white solid, 7.57 g, mp 70-72° C.

Combustion analysis: Found: C, 66.70; H, 7.42%; $C_{14}H_{18}O_4$ requires C, 67.09; H, 7.25%; 1H NMR (d6-DMSO): ÿ 12.1, bs, 1H (COOH); ÿ 7.54, dt, 1H, (H ortho to acetyl); ÿ 7.43, m, 2H (H's para to acetyl and OR); ÿ 7.20, dd, 1H (H ortho to OR); ÿ 4.02, t, 2H, (CH2 ÿ to O); ÿ 2.57, s, 3H (CH3 of acetyl); ÿ 2.24, t, 2H (CH2 ÿ to COOH); ÿ 1.73, p, 2H (CH2 ÿ to ArO or to COOR); ÿ 1.54, p, 2H (CH2 ÿ to ArO or to COOR), ÿ 1.46, p, 2H (CH2 in middle of chain).

Example 4

Preparation of 4-(2-methylbenzyloxy)butyric acid (Compound 3)

A suspension of 2-methylphenol (16.22 g, 0.15 mol), ethyl 4-bromobutanoate (33.80 g, 0.165 mol), and potassium carbonate (24.88 g, 0.18 mol) in 500 mL of 2-butanone was heated at reflux under nitrogen for 5 hours An additional 3 g of ethyl 4-bromobutanoate was added, and the reflux was continued for an additional 25 h. The reaction was allowed to cool to room temperature. Water and ethyl acetate were added. The organic product was extracted into the organic layer. The organic layer was separated and washed with water and brine. It was concentrated in vacuo to yield an oil. 200 mL of water and 150 mL of a 2N aqueous solution of NaOH was added to the oil. The mixture was stirred at room temperature overnight, and then heated at reflux for an hour. The mixture was cooled to room temperature and ice was added to chill the mixture to about 0° C. Slow addition of a solution of 2N hydrochloric acid solution (150 ml) caused an immediate precipitation. The resulting solid was collected by filtration, washed successively with water and with heptane. Drying in vacuo provided 22.18 g (76%) of the title compound as a white solid. Mp: 79-80° C. HPLC Rt 4.96 min.; 1H NMR (DMSO d6, 300 MHz) δ: 1.97 (m, 2H), 2.15 (s, 3H), 2.42 (t, 2H), 3.97 (t 2H), 6.82 (t, 1H), 6.88 (d, 1H), 7.10-7.16 (m, 2H), 12.20 (s, 1H). Anal. Calcd for $C_{11}H_{14}O_3$: C, 68.02; H, 7.27. Found: C, 68.04; H, 7.15.

Example 5

Preparation of 4-(3,4-dimethylphenoxy)-butyric acid (Compound 4)

3,4-Dimethylphenol (24.5 g, 0.2 mol) was dissolved in 125 ml of anhydrous ethanol. 75 ml of 21 wt % sodium ethoxide solution in ethanol (0.2 mol) was added to the solution. The mixture was stirred at room temperature for 10 min. Ethyl 4-bromobutyrate (40 g, 0.205 mol) was then added. The reaction mixture was refluxed at 80° C. for 24 h. The precipitate was filtered off. The filtrate was then mixed with a solution of sodium hydroxide (10 g, 0.25 mol) in 150 ml of water. The mixture was stirred at 70° C. for about 2 h, monitored with HPLC. It was diluted with 150 ml of water and acidified to pH 1. Oily precipitate formed immediately. It was collected by decanting the supernatant and washed with water twice (100 ml×2). The oily precipitate solidified after being kept in water at room temperature over night.

The precipitate was dissolved in 250 ml of water having pH 8-9. Any insoluble substance was filtered off. The filtrate was extracted with ethyl acetate twice (100 ml×2). The aqueous solution was acidified to pH 1. Precipitate formed immediately as oil, which solidified in about 2 h. It was collected by filtration, washed thoroughly with water and dried in air. 22.9 g of 4-(2,5-dimethylphenoxy)-butyrate were recovered. Melting point: 87-89° C. Combustion analysis: % C, 69.21 (Calc'd), 69.25 (Found); % H, 7.74 (Calc'd), 7.93 (Found); 1H NMR analysis (d6-DMSO): δ 6.99, d, 1H; 6.72, d, 1H; 6.62, q, 1H; 3.90, t, 2H; 2.36, t, 2H; 2.16, s, 3H, 2.12, s, 3H; 1.90, p, 2H.

Example 6

Preparation of 4-(2,3-Dimethylphenoxy)butyric acid (Compound 5)

2,3-Dimethylphenol (24.5 g, 0.2 mol) was dissolved in 125 ml of anhydrous ethanol. Seventy five (75) ml of 21 wt % sodium ethoxide solution in ethanol (0.2 mol) was added to the solution. The mixture solution was stirred at room temperature for 10 min. Ethyl 4-bromobutyrate (40 g, 0.205 mol) was then added to the solution. The reaction mixture was refluxed at 80° C. for 24 h. The precipitate was filtered of. The filtrate was then mixed with a solution of sodium hydroxide (10 g, 0.25 mol) in 150 ml of water. The mixture was stirred at 70° C. for about 2 hours, and monitored with HPLC. The mixture was diluted with 150 ml of water and acidified to pH 1. Oily precipitate formed immediately. The precipitate was collected by decanting the supernatant and washed with water twice (100 ml×2). The oily precipitate solidified after being kept in water at room temperature overnight.

The precipitate was dissolved in 250 ml of water at pH 8-9. Any insoluble substance was filtered off. The filtrate was extracted with ethyl acetate twice (100 ml×2). The aqueous solution was acidified to pH 1. Precipitate formed immediately as oil, which solidified in about 2 hours. The precipitate was collected by filtration, washed thoroughly with water and dried in air. 22.9 g of 4-(2,3-dimethylphenoxy)-butyrate were recovered. Melting point: 105-107° C. Combustion analysis (with a KF of 0.16): % C, 69.10 (Calc'd), 69.11 (Found); % H, 7.75 (Calc'd), 7.79 (Found); 1H NMR analysis (d6-DMSO): δ 7.00, t, 1H; 6.74, m, 2H; 3.94, t, 2H; 2.40, t, 2H; 2.20, s, 3H; 2.06, s, 3H; 1.95, p, 2H.

Example 7

Preparation of 4-(3-methylbenzyloxy)butyric acid (Compound 6)

A suspension of 3-methylphenol (200 g, 1.85 mol), ethyl 4-bromobutanoate (433 g, 2.11 mol), potassium hydroxide (155.7 g, 2.78 mol), 500 mL of water in 2500 mL of Dimethylsulfoxide (DMSO) in a 5-L flask was stirred at room temperature overnight. An additional 500 g water was added, and the reaction mixture was heated at 75° C. for 2 hours. Potassium hydroxide (155.7 g, 2.78 mol) was added. The reaction was stirred for an additional 30 min. The thick slurry was transferred in a 22-L flask. Addition of water (6 L) to the slurry with stirring caused the dissolution of the slurry. Concentrated HCl (300 mL) was slowly added. During the reaction, the temperature of the reaction mixture was maintained at about 36° C. with external cooling with ice. After the addition, the mixture was further cooled overnight to 10° C. The resulting solid was collected by filtration, washed with 100 mL of water, and dried with in-house vacuum for 2 days. Further drying high vacuum overnight afforded 311.88 g of the crude material. Recryallization in a mixture of ethanol (400 mL) and water (150 mL) yielded 290.94 g (81%) of the desired product as a solid. Mp: 53-54° C. HPLC Rt 5.13 min.; 1H NMR (DMSO d6, 300 MHz) δ: 1.88 (m, 2H), 2.22 (s, 3H), 2.33 (t, 2H), 3.89 (t, 2H), 6.62-6.72 (m, 3H), 7.10 (m, 1H), 12.20 (s, 1H). Anal. Calcd for C11H14O3: C, 67.82; H, 7.28. Found: C, 67.90; H, 7.36.

Example 8

Preparation of 4-(3-Fluorophenoxy)butyric acid (Compound 7)

A 1 L 3-neck round bottom flask equipped with a magnetic stirrer bar and a reflux condenser was charged with 17.17 g (150 mmol) of 3-fluorophenol, 33.82 g (165 mmol) of ethyl 4-bromobutyrate, 24.88 g, 180 mmol potassium carbonate and 600 mL of 2-butanone. The slurry heated to reflux. After stirring for 21 hr at reflux, the reaction mixture was cooled to 25° C., filtered and concentrated. The residue was taken up in of water and treated with 150 mL of 2N aqueous sodium hydroxide (300 mmol). The reaction mixture was heated to reflux for 30 min and cooled to 25° C. The brown solution was acidified with aqueous 150 ml of 2N hydrochloric acid. The resulting pink solid was isolated by filtration washing with hexanes to yield 25.04 g, mp 53-54° C. Combustion analysis: Found: C, 60.53; H, 5.79%; F, 9.84%; $C_{10}H_{11}FO_3$ requires C, 60.60; H, 5.59%; F, 9.59%; 1H NMR (d6-DMSO): δ 12.1, bs, 1H (COOH); δ 7.20, dd, 1H, (H para to OR); δ 6.7, m, 3H (aryl H's); δ 3.90, t 2H, ($CH_2$ α to O); δ 2.30, t, 2H ($CH_2$ α to COOR); δ 1.87, p, 2H ($CH_2$ β to ArO and COOH).

Example 9

Preparation of 4-(2-Chlorophenoxy)butanoic acid

A 500 mL 3-neck round bottom flask equipped with a magnetic stirrer bar and a reflux condenser was charged with 12.88 g (100 mmol) of 2-chlorophenol, 22.54 g (110 mmol) of ethyl 4-bromobutyrate, 16.59 g, 120 mmol potassium carbonate and 350 mL of 2-butanone. The slurry was heated to reflux. After stirring for 21 hr at reflux, the reaction mixture was cooled to 25° C., filtered and concentrated. The residue was taken up in 400 mL of water and treated with 100 mL of 2N aqueous sodium hydroxide (200 mmol). The reaction mixture was heated to reflux for 120 min and cooled to 25° C. The resulting solution was acidified with aqueous 105 ml of 2N hydrochloric acid. The resulting white solid was isolated by filtration by washing with hexanes to yield 20.68 g of 4-(2-Chlorophenoxy)butanoic acid. Mp 85-87° C. Combustion analysis: Found: C, 55.97; H, 5.13%; Cl, 16.55%; $C_{10}H_{11}ClO_3$ requires C, 55.96; H, 5.17%; Cl, 16.52%; 1H NMR (d6-DMSO): δ 12.1, bs, 1H (COOH); δ 7.42, dd, 1H, (H ortho to Cl); δ 7.29, t, 1H (H para to Cl); δ 7.13, d, 1H, (H ortho to OR); δ 6.95, t, 1H (H para to OR); δ 4.07, t, 2H, ($CH_2$ α to O); δ 2.44, t, 2H (CH2 α to COOH); δ 1.98, p, 2H (CH2 β to ArO and COOH).

Example 10

Preparation of 8-[2-(4-Chlorophenoxy)-2-methylpropionyl]-aminocaprylic acid 8-aminooctanoic acid (3.2 g, 20 mmol) and sodium hydroxide (2.0 g, 50 mmol) were dissolved in 50 mL water.

The solution was cooled in an ice bath. 2-methyl-2-(4-chlorophenoxy)propionyl chloride (4.6 g, 20 mmol) was then added to the mixture dropwise while stirring vigorously. The mixture stirred at 25° C. for 3 hours. The cloudy basic solution was extracted with ethyl acetate (20 ml×1) producing a clear solution. The solution was acidified to pH 1 with aqueous hydrochloric acid at 0° C. A syrupy precipitate formed. The syrupy precipitate solidified after 3 hours at 0° C. The resulting solid was isolated by filtration and dried in the air to afford 6.4 g of the crude product. Recrystallization from ethyl acetate/n-hexane yielded 5.9 g (84.5%) of the desired product Melting point: 94-96° C., HPLC Rt 6.42 min. Combustion analysis: Found: C, 60.88%; H, 7.42%, N, 3.87%, Cl, 9.96%; Calculated: C, 60.75%; H, 7.36%; N, 3.94%; Cl, 9.96%. 1H NMR analysis (d6-DMSO): δ 12.0, broad s, 1H, (COOH), δ 8.1, t 1H, (NH); δ 7.3, d, 2H (aryl H's); δ 6.85, d, 2H (aryl H's); δ 3.1, m, 2H (CH2 α NH); δ 2.20, t, 2H(CH2 α COOH); δ 1.4, m 10H (rest of CH2's); δ 1.2, m, 6H (CH3's).

Example 11

Preparation of 6-[2-(4-Chlorophenoxy)-2-methylpropionyl]-aminohexanoic acid

6-Aminohexanoic acid (3.0 g, 23 mmol) and sodium hydroxide (2.0 g, 50 mmol) were dissolved in 50 mL water. The solution was cooled in an ice bath, and 2-methyl-2-(4-chlorophenoxy)-propionyl chloride (4.6 g, 20 mmol) was added to the mixture dropwise while stirring vigorously. The mixture stirred at 25° C. for 3 hours. The cloudy basic solution was extracted with ethyl acetate (20 ml×1) producing a clear solution. It was acidified to pH 1 with aqueous hydrochloric acid at 0° C. A syrupy precipitate formed. The syrupy precipitate solidified after 3 hours at 0° C. The resulting solid was isolated by filtration and dried in the air. Recrystallization from ethyl acetate/n-hexane yielded 5.4 g (83.0%) of the desired product. Mp: 61-63° C. HPLC Rt 5.40 min.; Combustion analysis: Pound: C, 58.62%; H, 6.35%; N, 4.17%; Calculated: C, 58.62%; H, 6.35%; N, 4.27%; 1H NMR analysis (d6-DMSO): δ 12.0, broad s, 1H (COOH); δ 8.1, t, 1H (NH); δ 7.3, d, 2H (aryl H); δ 6.85, d, 2H (aryl H); δ 3.1, m, 2H (CH2 α NH); δ 2.15, t, 2H (CH2 α COOH); δ 1.4, s, 6H (CH3's); δ 1.4, m, 4H (CH2's); δ 1.2, m, 2H (middle CH2).

Example 12

Preparation of 4-(4-Fluoro-2-methyl-phenoxy)-butyric aid

A 200 ml 3-neck round bottom flask equipped with a magnetic stirrer bar and a reflux condenser was charged with 4.42 g (34 mmol) of 2-fluoro-4-methylphenol, 7.58 g (37 mmol) ethyl 4-bromobutyrate, 5.67 g (41 mmol) potassium carbonate and 130 mL of 2-butanone. After stirring for 20 hr at reflux, the reaction mixture was cooled to 25° C. and diluted with ethyl acetate and distilled water. The layers were separated. The organic layer was washed with distilled water and brine. It was dried over potassium carbonate, transferred to a 1000 ml flask and concentrated. The precipitate was dissolved in distilled water. The solution was mixed with 40 ml (80 mmol) 2N aqueous sodium hydroxide. The reaction mixture was heated to reflux for 30 min until the ester was hydrolyzed (determined by HPLC). The mixture was cooled to 25° C., using an ice bath. The amber solution was acidified with 45 ml of 2N aqueous hydrochloric acid. The resulting white solid was isolated by filtration washing with water twice followed by hexanes twice to yield 4.88 g (68%) of the desired product. Combustion analysis: Found: C, 62.07%; H, 6.4%; Calculated: C, 62.26%; H, 6.4%; 1H NMR (d6-DMSO): δ12.1, s, 1H (COOH); δ 6.8-6.9, m, 3H (aryl H); δ3.8, t, 2H, (CH2 α to ArO); δ2.3, t, 2H (CH2 α COOH); δ 2.1, s, 3H, (CH3 meta to F); δ1.8, m, 2H (CH2 β to COOH).

Example 13

Preparation of 4-(2-Fluoro-5-methyl-phenoxy)-butyric acid

A 200 ml 3-neck round bottom flask equipped with a magnetic stirrer bar and a reflux condenser was charged with 4.99 g (40 mmol) of 2-fluoro-5-methyl phenol, 9.01 g (44 mmol) of ethyl 4-bromobutyrate, 6.63 g (48 mmol) potassium carbonate and 120 ml of 2-butanone. The slurry heated to reflux. After stirring for 14.5 hr at reflux, the reaction mixture was cooled to 25° C., filtered and concentrated. The residue was taken up in water (200 ml) and treated with 42 ml (84 mmol) 2N aqueous sodium hydroxide. The reaction mixture was heated to reflux for 2 hours and cooled to 25° C. The yellow solution was acidified with 45 ml 2N aqueous hydrochloric acid. The resulting white solid was isolated by filtration washing with twice with water then twice with hexanes to yield 7.64 g (90%), mp 62-64° C. Combustion analysis: Found: C, 62.2%; H, 6.19%; Calculated: C, 62.26%; H, 6.17%; 1H NMR analysis (d6-DMSO): δ 12.2, broad s, 1H, (COOH); δ7.0, m, 2H (aryl H); δ 6.7, s, 1H (aryl H); δ 4.0, t, 2H (CH$_2$ α ArO); δ 2.4, t, 2H (CH$_2$ α COOH); δ 2.21, s, 3H (CH$_3$ para F); δ 1.90, m, 2H (CH$_2$ β COOH).

Example 14

Preparation of 5-(2-Chloro-phenoxy)-pentanoic acid

A 500 ml 3-neck round bottom flask equipped with a magnetic stirrer bar and a reflux condenser was charged with 12.86 (100 mmol) 2-chloro phenol, 23.49 g (110 mmol) ethyl 5-bromovalerate, 16.60 g (120 mmol) potassium carbonate and 300 mL of 2-butanone. The slurry heated to reflux. After stirring for 20 hr at reflux (completeness confirmed by HPLC), the reaction mixture was cooled to 25° C., filtered and concentrated. The residue was taken up in of water (300 ml) and treated with 100 ml (200 mmol) 2N aqueous sodium hydroxide. This suspension was heated to reflux for 2 hours until it turned to a solution. The solution was cooled to 25° C. Ice was added to further cool to 0° C. The yellow solution was acidified with aqueous 105 ml 2N hydrochloric acid. The resulting white solid was isolated by filtration washing with water twice then hexanes twice to yield 22.24 g (97%) of the desired product, Mp 71-72° C. Combustion analysis: Found: C, 57.66%; H, 5.82%, Cl, 15.5%; Calculated: C, 57.78%; H, 5.73%; Cl, 15.5%; 1H NMR (d6-DMSO): δ 12.1, broad s, 1H (COOH); δ 7.40, dd, 1H (aryl H); δ 7.25, m, 1H (aryl H); δ 7.10, dd, 1H (aryl H); δ 6.9, m, 1H (aryl A); δ 4.0, t, 2H (CH2 α ArO); δ 2.3, t, 2H (CH2 α COOH); δ 1.7, m, 4H (rest of CH2's).

Other compounds contained herein can be prepared by similar methods known to those skilled in the art.

Example 15

Oral Delivery of Insulin in Rats

Human recombinant insulin (ICN Biomedicals, Aurora, Ohio) was dissolved in deionized water (ph~6.5) to obtain stock insulin solutions having a concentration of 15 mg/ml.

Sodium salts of the delivery agent compounds shown below in table 1 dissolved in deionized water to obtain a 200 mg/ml delivery agent solution. The free acid form of delivery agent as converted to the sodium salt by adding one equivalent of sodium hydroxide. Solutions were vortexted, sonicated, and heated. If necessary, additional sodium hydroxide was added in μl quantities to achieve uniform solubility in the delivery agent solutions. Solutions were adjusted to a pit of 3.5-8.5 by the addition of either hydrochloric acid or sodium hydroxide, as appropriate. The insulin stock solution was then added to the delivery agent solutions to obtain an administration solution ultimately having an insulin concentration of 0.5 mg/ml. After solubilization and drug addition, administration solutions were brought to a final volume by the addition of deionized water.

Insulin was administered to male, Sprague-Dawley rats either alone or in combination with delivery agent by oral gavage (PO). Rats, weighing 0.22 to 0.27 kg, were fasted for 18-24 hours prior to dosing. A Rusch 8 French catheter was cut to 11 cm in length and adapted to fit a 1 ml syringe. The syringe was filled with dosing solution and the catheter was inserted into the at mouth and fed down the esophagus (10.0 cm). The dosing solution was delivered by pressing the syringe plunger while holding the rat in an upright position. The doses of delivery agent and insulin were 200 mg/kg and 0.5 mg/g, respectively unless noted otherwise in Table 1. The dose volume was 1 ml/g.

Immediate to each blood sampling point, rats were exposed briefly (~10 seconds) to carbon dioxide until prostrate. A 77-nun capillary tube was inserted into the retroorbital sinus. Typically, blood samples were collected prior to dosing (time=0) and at 15, 30, 45, and 60 minutes after dosing.

To determine the pharmacodynamic response, a hand-held glucometer (OneTouch Ultra, LifeScan—Johnson & Johnson, New Brunswick, N.J.) was used to measure whole blood glucose after administration of insulin or insulin and delivery agent. After discarding the first drop of blood, a small sample (~5-10 μls) was touched to the glucometer test strip (OneTouch Ultra, LifeScan) and a blood glucose reading was generated by the meter. Samples at the times indicated below in Table 1 after dosing.

The following results were obtained:

TABLE 1

Oral Delivery of Insulin in Rats

| Delivery Agent Compound | Average Glucose Reduction - (5 rats/experiment) | Amount of Insulin (mg/kg of rat weight) | Amount of Delivery Agent (mg/kg of rat weight) | Time period (minutes) |
|---|---|---|---|---|
| 1 | −17.2% | 0.5 | 200 | 30 |
| 1 | −63.3% | 0.5 | 200 | 30 |
| 1 | −78.4% | 0.5 | 200 | 45 |
| 1 | −8.8% | 0.5 | 25 | 30 |
| 1 | −51.4% | 0.5 | 50 | 30 |
| 1 | −31.4% | 0.5 | 100 | 30 |
| 1 | −66.4% | 0.5 | 200 | 45 |
| 1 | −16.1% | 0.05 | 200 | 15 |
| 1 | −13.0% | 0.10 | 200 | 30 |
| 1 | −34.0% | 0.3 | 200 | 45 |
| 1 | −45.4% | 0.5 | 200 | 45 |
| 1 | −0.8% | 0.5 | 25 | 30 |
| 1 | −5.7% | 0.5 | 50 | 30 |
| 1 | −60.6% | 0.5 | 100 | 45 |
| 1 | −57.0% | 0.5 | 200 | 30 |
| 1 | −69.8% | 0.5 | 200 | 45 |
| 1 | −41.5% | 0.5 | 200 | 45 |
| 1 | −29.7% | 0.5 | 200 | 30 |
| 1 | −55.5% | 0.5 | 200 | 30 |
| 2 | −53.6% | 0.5 | 200 | 45 |
| 2 | −25.8% | 0.5 | 25 | 45 |
| 2 | −30.2% | 0.5 | 50 | 45 |
| 2 | −50.8% | 0.5 | 100 | 45 |
| 2 | −18.7% | 0.5 | 200 | 45 |
| 2 | −1.1% | 0.5 | 200 | 45 |
| 2 | −13.3% | 0.5 | 200 | 45 |
| 2 | −29.4% | 0.5 | 200 | 45 |
| 2 | −30.0% | 0.5 | 200 | 45 |
| 2 | +1.6% | 0.5 | 200 | 45 |
| 2 | +8.2% | 0.5 | 200 | 45 |
| 2 | −15.9% | 0.5 | 200 | 45 |
| 2 | −41.7% | 0.5 | 200 | 45 |
| 3 | −51.5% | 0.5 | 200 | 45 |
| 3 | −72.8% | 0.5 | 200 | 45 |
| 3 | −43.2% | 0.5 | 200 | 45 |
| 3 | −49.1% | 0.5 | 200 | 45 |
| 3 | −51.5% | 0.5 | 200 | 45 |
| 4 | −55.9% | 0.5 | 200 | 45 |
| 4 | −56.8% | 0.5 | 200 | 45 |
| 4 | −55.1% | 0.5 | 200 | 45 |
| 4 | −2.2% | 0.5 | 200 | 45 |
| 4 | −6.7% | 0.5 | 200 | 45 |
| 4 | −8.3% | 0.5 | 200 | 45 |
| 4 | −32.7% | 0.5 | 200 | 45 |
| 4 | −28.7% | 0.5 | 200 | 45 |
| 5 | −42.8% | 0.5 | 200 | 45 |
| 5 | −66.3% | 0.5 | 200 | 45 |

TABLE 1-continued

Oral Delivery of Insulin in Rats

| Delivery Agent Compound | Average Glucose Reduction - (5 rats/experiment) | Amount of Insulin (mg/kg of rat weight) | Amount of Delivery Agent (mg/kg of rat weight) | Time period (minutes) |
|---|---|---|---|---|
| 5 | −52.3% | 0.5 | 200 | 45 |
| 6 | −36.0% | 0.5 | 200 | 30 |
| 6 | −61.2% | 0.5 | 200 | 30 |
| 6 | −42.9% | 0.5 | 200 | 45 |
| 6 | −19.3% | 0.5 | 25 | 30 |
| 6 | −11.9% | 0.5 | 50 | 30 |
| 6 | −47.9% | 0.5 | 100 | 30 |
| 6 | −14.4% | 0.5 | 200 | 60 |
| 6 | −3.7% | 0.5 | 25 | 30 |
| 6 | −28.7% | 0.5 | 50 | 30 |
| 6 | −63.7% | 0.5 | 100 | 30 |
| 6 | −79.0% | 0.5 | 200 | 45 |
| 6 | −4.4% | 0.5 | 25 | 30 |
| 6 | −19.9% | 0.5 | 50 | 30 |
| 6 | −39.3% | 0.5 | 100 | 45 |
| 6 | −41.9% | 0.5 | 200 | 30 |
| 6 | −33.9% | 0.5 | 200 | 30 |
| 6 | −44.7% | 0.5 | 200 | 30 |
| 6 | −55.3% | 0.5 | 200 | 30 |
| 6 | −30.9% | 0.25 | 100 | 45 |
| 7 | −65.6 | 0.5 | 200 | 45 |
| 7 | −68.0% | 0.5 | 200 | 45 |
| 7 | −61.5% | 0.5 | 200 | 45 |
| 7 | −16.6% | 0.5 | 200 | 45 |
| 8 | −78.0% | 0.5 | 200 | 45 |
| 8 | −25.4% | 0.5 | 200 | 45 |
| 8 | −52.0% | 0.5 | 200 | 45 |
| 8 | −34.0% | 0.5 | 200 | 45 |
| 10 | 2.5% | 0.5 | 200 | 30 |
| 11 | −−63.7% | 0.5 | 200 | 30 |
| 11 | −78.0% | 0.5 | 200 | 45 |
| 12 | −78.8% | 0.5 | 200 | 30 |
| 12 | −81.5% | 0.5 | 200 | 30 |
| 12 | −70.4% | 0.5 | 200 | 30 |
| 12 | −47.9% | 0.5 | 100 | 30 |
| 12 | −25.7% | 0.5 | 50 | 60 |
| 12 | −13.1% | 0.5 | 25 | 60 |
| 12 | −41.0% | 0.25 | 100 | 30 |
| 12 | −82.1% | 0.5 | 200 | 30 |
| 13 | −36.5% | 0.5 | 200 | 30 |
| 13 | −48.4% | 0.5 | 200 | 30 |
| 13 | −−63.7% | 0.5 | 200 | 30 |

Example 16

Delivery of Argatroban in Rats

Argatroban was administered to rats orally with and without a delivery agent, and intravenously without a delivery agent. The oral dose of argatroban used was 4 mg/kg body weight. The dose of the sodium salt of delivery agent (4-(2, 5-Dimethylphenoxy)butyric acid) was 200 mg/kg body weight. The ravenous dose of argatroban used was 1 mg/kg body weight A baseline blood sample was taken from the retroorbital sinus prior to dosing (time=0). Blood samples were drawn from the retroorbital sinus at various time points after dosing. Argatroban was administered to male, Sprague-Dawley rats either alone or in combination with delivery agent by oral gavage (PO). Typically, rats (generally weighing 0.22 to 0.27 kg) were fasted for 18-24 hours prior to dosing. A Rusch $ French catheter was cut to 11 cm in length and adapted to fit a 1 ml syringe. The syringe was filled with dosing solution and the catheter was inserted into the rat mouth and fed down the esophagus (10.0 cm). The dosing solution was delivered by pressing the syringe plunger while holding the rat in an upright position. The doses of delivery agent and argatroban were 200 mg/kg and 4.0 mg/kg, respectively. The dose volume was 1 ml/kg. For intravenous dosing the dose of argatroban was 1 mg/kg and a 1 ml/kg final dose volume was also used. Immediate to each blood sampling point, rats were exposed briefly (~10 seconds) to carbon dioxide until prostrate. A 77-mm capillary tube was inserted into the retroorbital sinus. Blood samples were collected prior to dosing (time=0) and at 10, 20, and 40 minutes after dosing.

Figure 2:
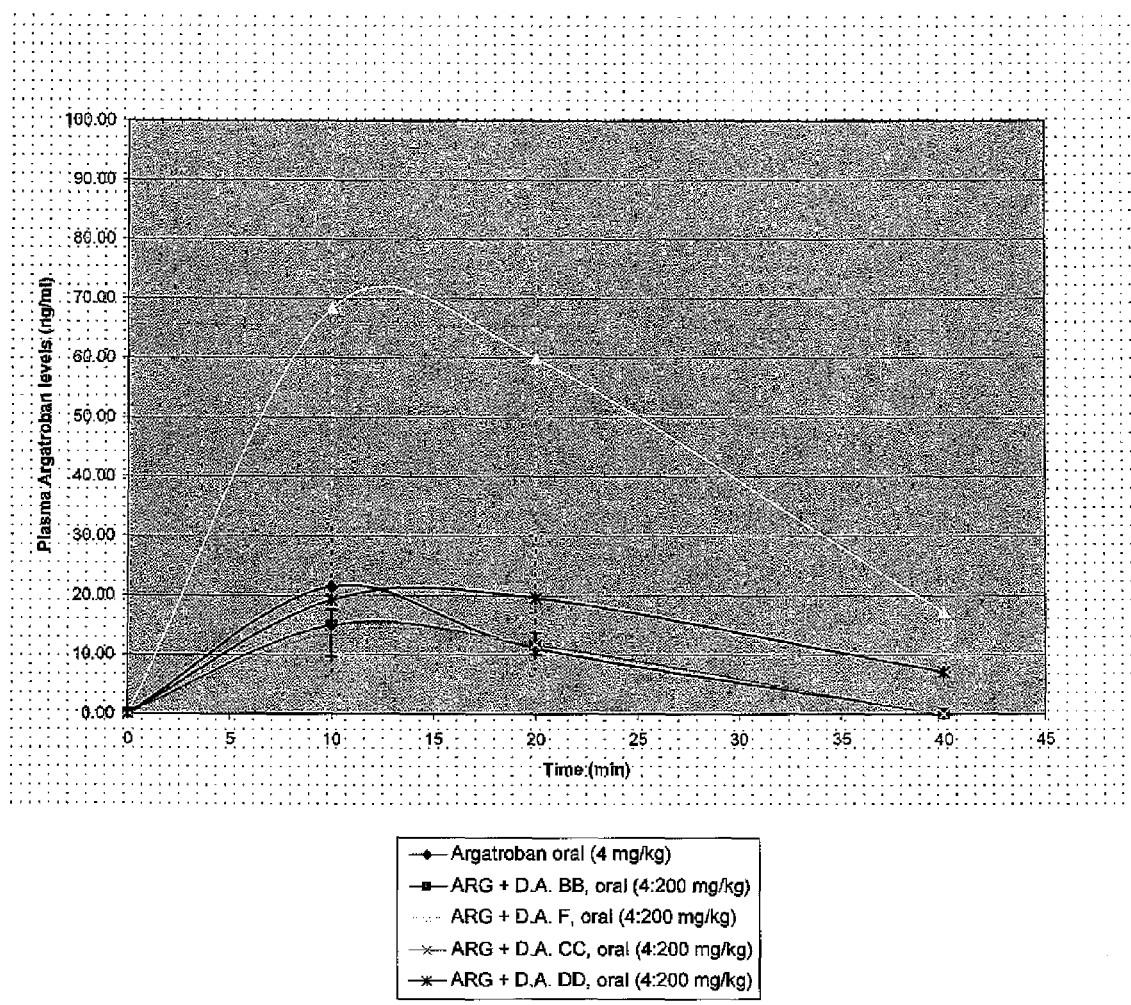
Figure 3:
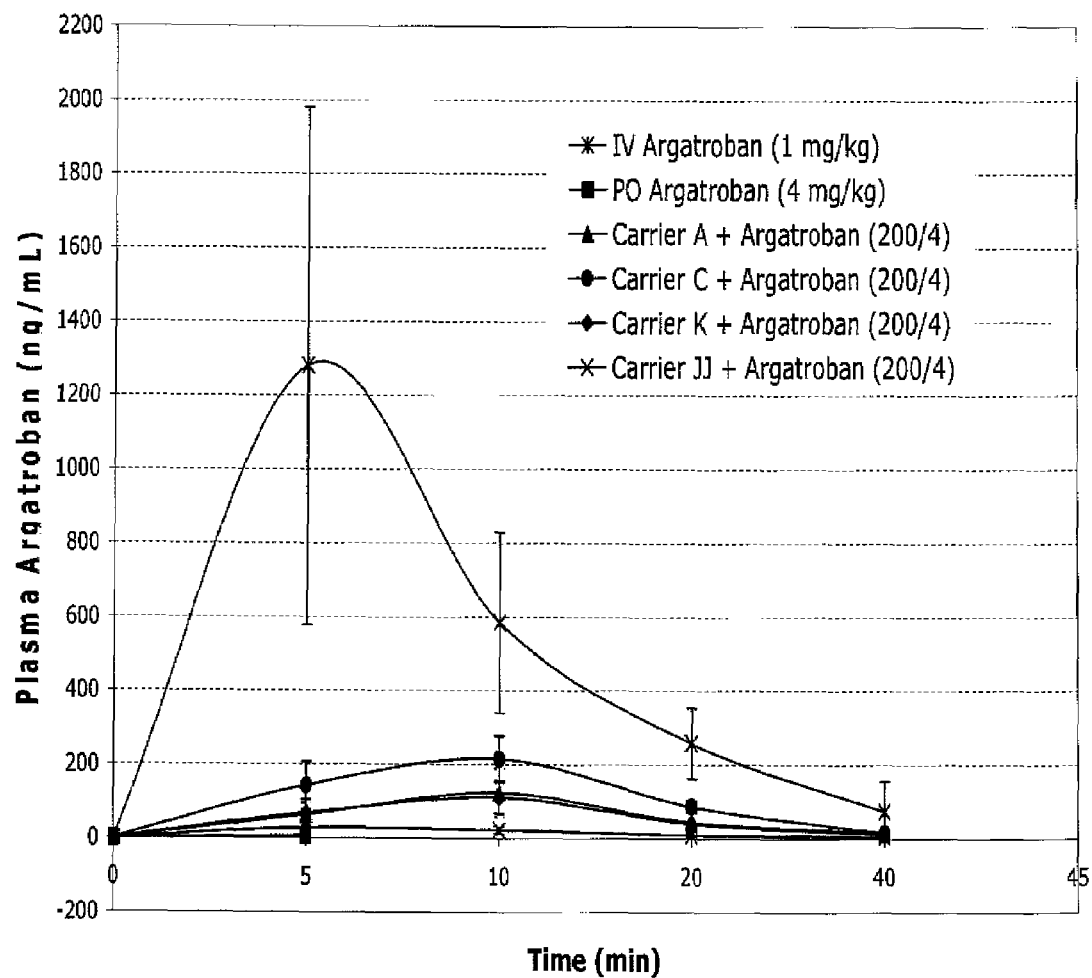
Figure 4:
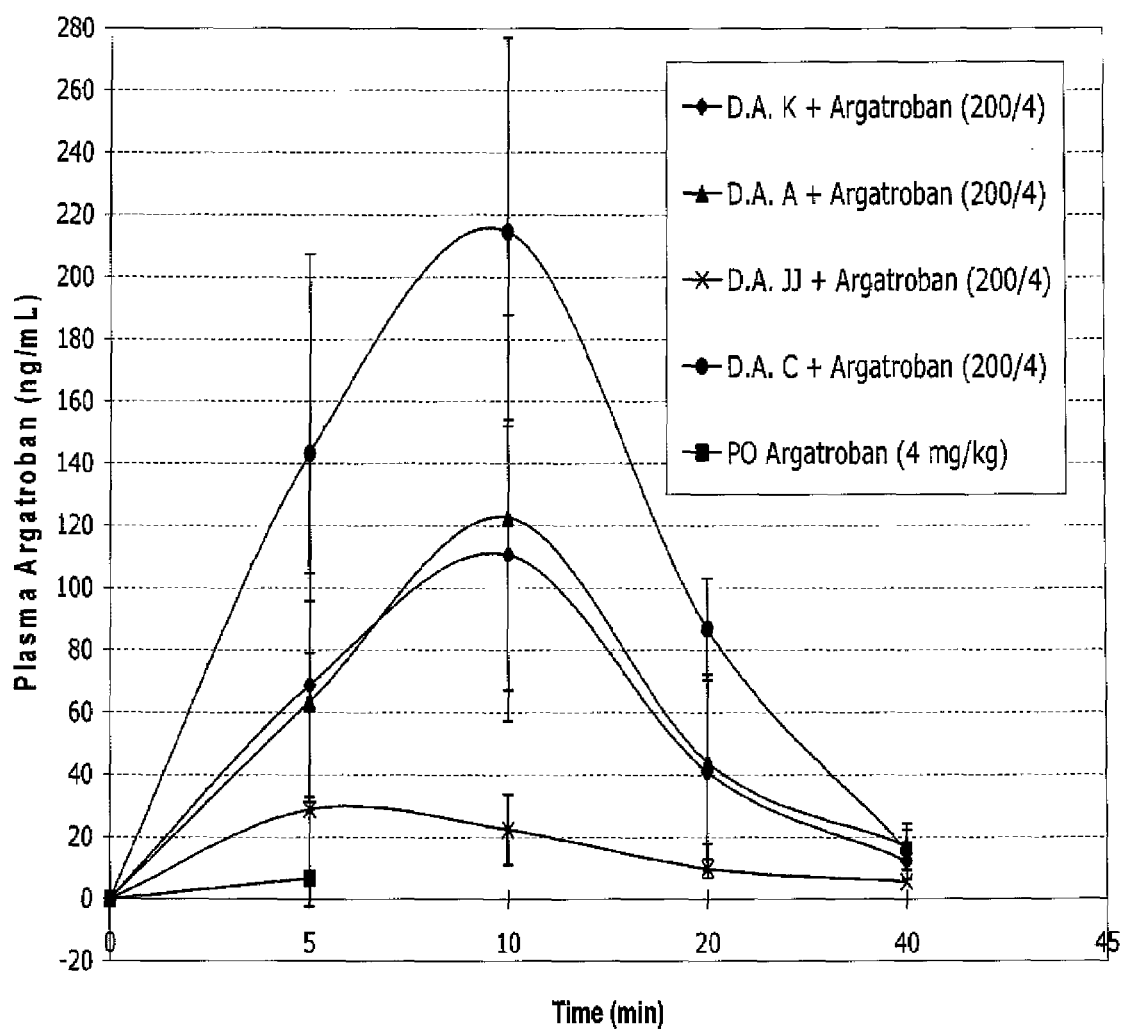
Figure 5:
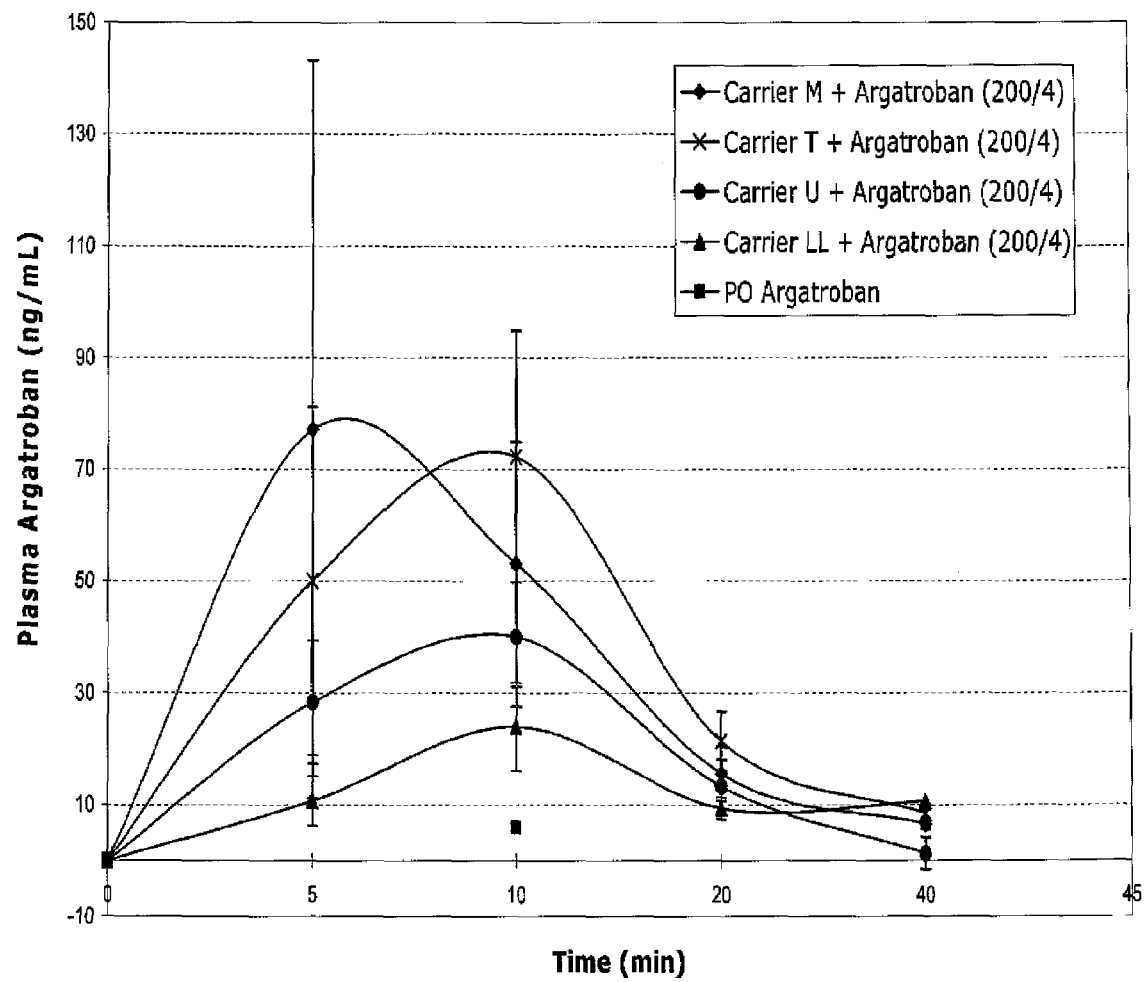
Figure 6:
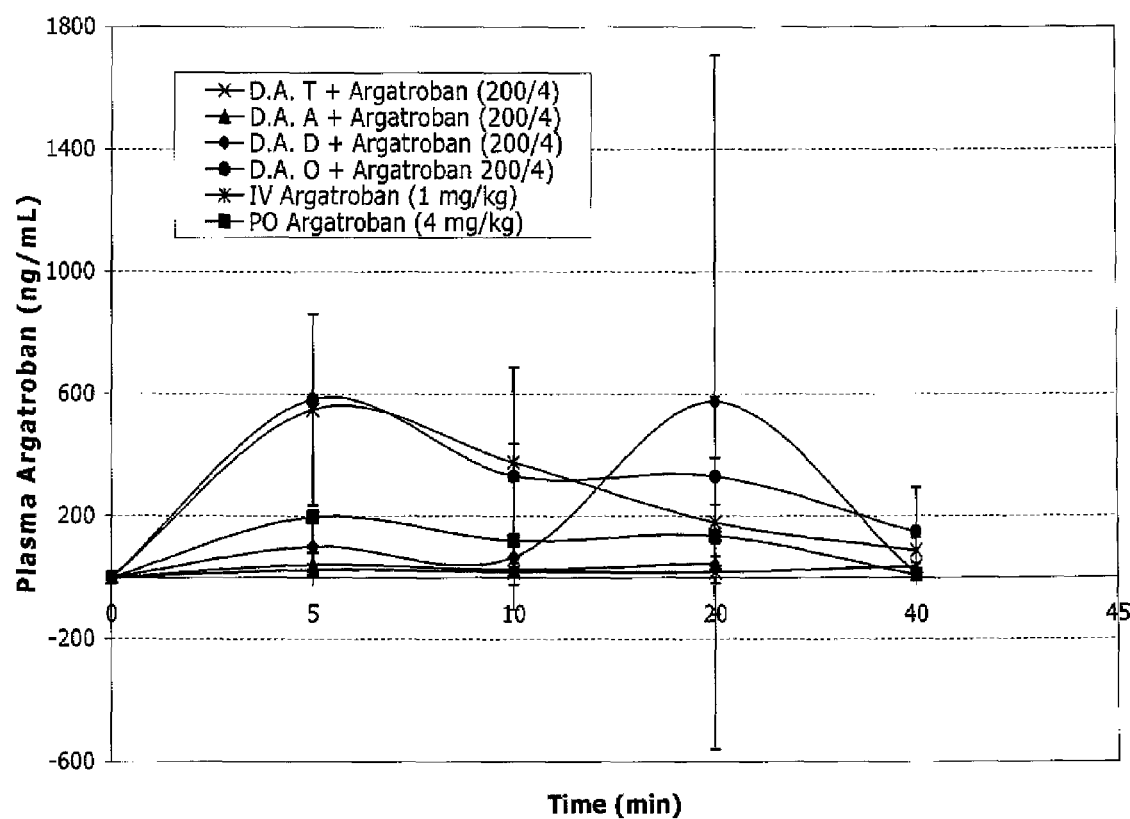

The argatroban plasma concentrations were determined at Glaxo Smith Kline via HPLC assay. The results are shown in FIGS. 1-6.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A delivery agent compound selected from the group consisting of:

Compound 2

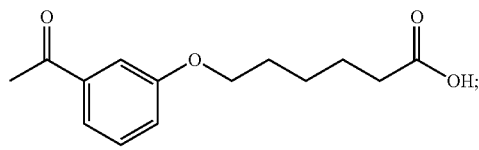

Compound 9

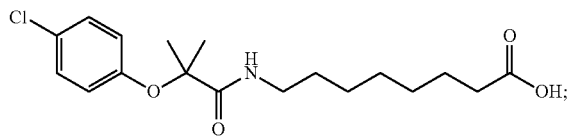

Compound 11

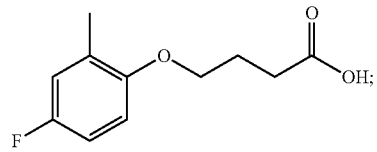

Compound 12

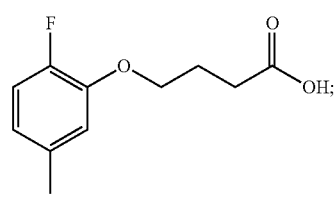

and pharmaceutically acceptable salts thereof.

2. The delivery agent compound of claim 1, wherein the delivery agent is

Compound 2

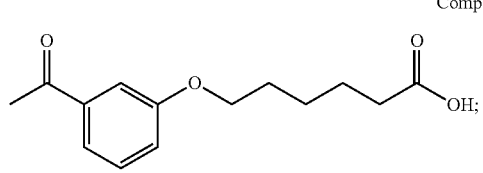

or a pharmaceutically acceptable salt thereof.

3. The delivery agent compound of claim 1, wherein the delivery agent is

Compound 9

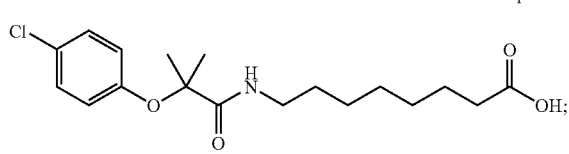

or a pharmaceutically acceptable salt thereof.

4. The delivery agent compound of claim 1, wherein the delivery agent is

Compound 11

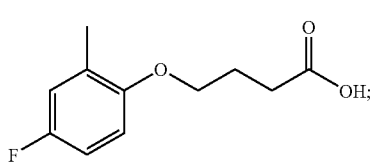

or a pharmaceutically acceptable salt thereof.

5. The delivery agent compound of claim 1, wherein the delivery agent is

Compound 12

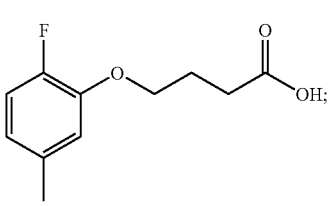

or a pharmaceutically acceptable salt thereof.

6. A pharmaceutical composition comprising
(A) a therapeutically effective amount of a biologically active agent;
(B) at least one compound selected from the group consisting of Compound 2

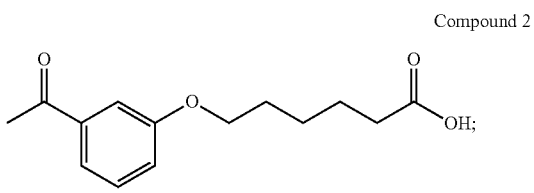 [SMILES: CC(=O)c1cccc(OCCCCCC(=O)O)c1]

Compound 4

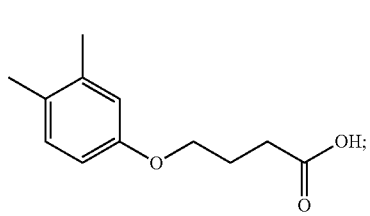

Compound 7

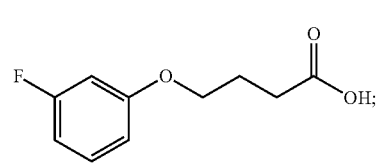

Compound 9

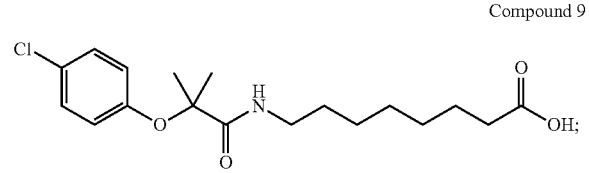 [SMILES: CC(C)(Oc1ccc(Cl)cc1)C(=O)NCCCCCCCC(=O)O]

-continued

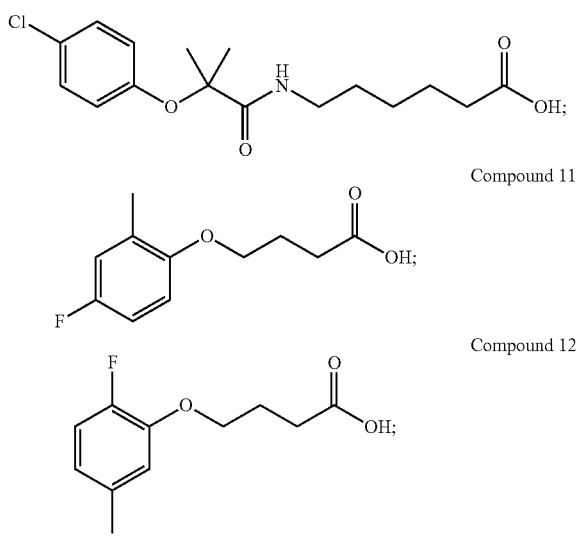

and pharmaceutically acceptable salts thereof; and
(C) a pharmaceutically acceptable excipient,
wherein the biologically active agent is selected from BIBN-4096BS, growth hormone releasing factor, interferons, interleukin-1, interleukin-2, insulin, insulin-like growth factor (IGF), heparin, heparinoids, dermatans, chondroitins, calcitonin, erythropoietin (EPO), atrial naturetic factor, CPHPC, monoclonal antibodies, somatostatin, octreotide, adrenocorticotropin, gonadotropin releasing hormone, oxytocin, leutinizing-hormone releasing-hormone, follicle stimulating hormone, glucocerebrosidase, thrombopoeitin, filgrastim, GM-CSF5, prostaglandins, cyclosporin, vasopressin, cromolyn sodium, sodium chromoglycate, disodium chromoglycate, vancomycin, gallium nitrate, glucagon, DPP-4 inhibitors, peptide YY, desferoxamine (DFO), parathyroid hormone (PTH), glucagon-like peptide 1 (GLP-I), argatroban; and any combination thereof.

7. The pharmaceutical composition of claim 6, wherein the biologically active agent is selected from the group consisting of insulin, leutenizing-hormone releasing hormone, GLP-1, heparin, recombinant human growth hormone, argatroban, and any combination thereof.

8. The pharmaceutical composition of claim 6, wherein the biologically active agent is argatroban.

9. The pharmaceutical composition of claim 6, wherein the biologically active agent is insulin.

10. The pharmaceutical composition of claim 6, wherein the biologically active agent is human growth hormone.

11. The pharmaceutical composition of claim 6, wherein the growth hormone is human growth hormone, recombinant human growth hormone (rhGH), bovine growth hormone or porcine growth hormone.

12. The pharmaceutical composition of claim 6, wherein the calcitonin is salmon calcitonin, eel calcitonin or human calcitonin.

13. The pharmaceutical composition of claim 6, wherein the insulin is porcine insulin, bovine insulin, human insulin or human recombinant insulin.

14. The pharmaceutical composition of claim 6, wherein the heparin is unfractionated heparin, low molecular weight heparin, very low molecular weight heparin or ultra low molecular weight heparin.

15. The pharmaceutical composition of claim 6, wherein the insulin-like growth factor is IGF-I.

16. A dosage unit form comprising a pharmaceutical composition of claim 6

17. The dosage unit form of claim 16, wherein the dosage unit form is a tablet or capsule.

18. A pharmaceutical composition comprising
(A) a therapeutically effective amount of a biologically active agent;
(B) a compound selected from:

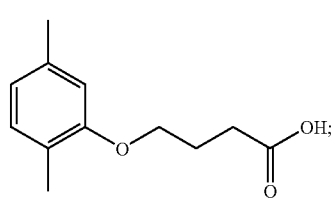

and pharmaceutically acceptable salts thereof; and
(C) a pharmaceutically acceptable excipient;
wherein the biologically active agent is selected from calcitonin, insulin, GLP-1, heparin, argatroban, and any combination thereof.

19. A pharmaceutical composition comprising
(A) a therapeutically effective amount of a biologically active agent;
(B) a compound selected from:

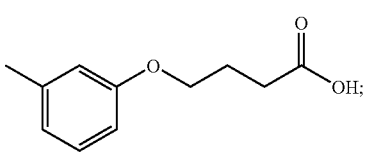

and pharmaceutically acceptable salts thereof; and
(C) a pharmaceutically acceptable excipient;
wherein the biologically active agent is selected from calcitonin, insulin, GLP-1, heparin, argatroban; and any combination thereof.

20. A pharmaceutical composition comprising
(A) a therapeutically effective amount of a biologically active agent;
(B) a compound selected from:

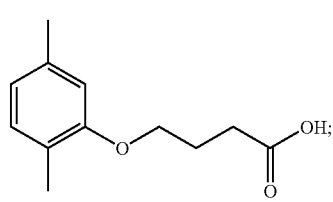

and pharmaceutically acceptable salts thereof; and
(C) a pharmaceutically acceptable excipient;
wherein the biologically active agent is selected from BIBN-4096BS, growth hormone releasing factor, interferons, interleukin-1, interleukin-2, insulin, insulin-like growth factor (IGF), heparin, heparinoids, dermatans, chondroitins, calcitonin, erythropoietin (EPO), atrial naturetic factor, CPHPC, monoclonal antibodies, somatostatin, octreotide, adrenocorticotropin, gonadotropin releasing hormone, oxytocin, leutinizing-hormone releasing-hormone, follicle stimulating hormone, glucocerebrosidase, thrombopoeitin, filgrastim, GM-CSF5, prostaglandins, cyclosporin, vasopressin, cromolyn sodium, sodium chromoglycate, disodium chromoglycate, vancomycin, gallium nitrate, glucagon, DPP-4 inhibitors, peptide YY, desferoxamine (DFO), parathyroid hormone (PTH), glucagon-like peptide 1 (GLP-I), argatroban; and any combination thereof.

21. A pharmaceutical composition comprising
(A) a therapeutically effective amount of a biologically active agent;
(B) a compound selected from:

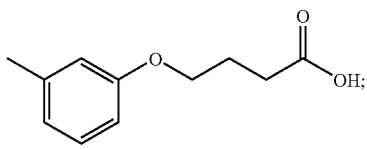

Compound 6 and pharmaceutically acceptable salts thereof; and (C) a pharmaceutically acceptable excipient;
wherein the biologically active agent is selected from BIBN-4096BS, growth hormone releasing factor, interferons, interleukin-1, interleukin-2, insulin, insulin-like growth factor (IGF), heparin, heparinoids, dermatans, chondroitins, calcitonin, erythropoietin (EPO), atrial naturetic factor, CPHPC, monoclonal antibodies, somatostatin, octreotide, adrenocorticotropin, gonadotropin releasing hormone, oxytocin, leutinizing-hormone releasing-hormone, follicle stimulating hormone, glucocerebrosidase, thrombopoeitin, filgrastim, GM-CSF5, prostaglandins, cyclosporin, vasopressin, cromolyn sodium, sodium chromoglycate, disodium chromoglycate, vancomycin, gallium nitrate, glucagon, DPP-4 inhibitors, peptide YY, desferoxamine (DFO), parathyroid hormone (PTH), glucagon-like peptide 1 (GLP-I), argatroban; and any combination thereof.

22. The composition according to claim 20, wherein the biologically active agent is selected from calcitonin, insulin, PTH, GLP-1, heparin, argatroban; and any combination thereof.

23. The composition according to claim 21, wherein the biologically active agent is selected from calcitonin, insulin, PTH, GLP-1, heparin, argatroban; and any combination thereof.

* * * * *